United States Patent
Seibl et al.

(10) Patent No.: US 8,574,611 B2
(45) Date of Patent: Nov. 5, 2013

(54) COMPOSITE BONE REPAIR MATERIAL

(75) Inventors: Reinhart Seibl, Zurich (CH); Aaldert Rens Molenberg, Binningen (CH); Astrid Sylvia Neidhardt, Thalwil (CH); Nienke Beuling, Delft (NL)

(73) Assignee: Straumann Holding AG, Basel (CH)

( * ) Notice: Subject to any disclaimer, the term of this patent is extended or adjusted under 35 U.S.C. 154(b) by 246 days.

(21) Appl. No.: 12/667,496

(22) PCT Filed: Jun. 30, 2008

(86) PCT No.: PCT/EP2008/005340
§ 371 (c)(1),
(2), (4) Date: Jul. 6, 2010

(87) PCT Pub. No.: WO2009/007034
PCT Pub. Date: Jan. 15, 2009

(65) Prior Publication Data
US 2010/0292146 A1    Nov. 18, 2010

(30) Foreign Application Priority Data

Jul. 12, 2007  (EP) .................................. 07013645

(51) Int. Cl.
*A61K 9/00* (2006.01)
(52) U.S. Cl.
USPC ........... 424/422; 424/423; 424/523; 523/113; 523/115
(58) Field of Classification Search
None
See application file for complete search history.

(56) References Cited

U.S. PATENT DOCUMENTS

| | | |
|---|---|---|
| 4,610,692 A * | 9/1986 | Eitenmuller et al. ......... 424/422 |
| 5,368,859 A | 11/1994 | Dunn et al. |
| 5,702,449 A | 12/1997 | McKay |
| 5,863,984 A | 1/1999 | Doillon et al. |
| 6,039,762 A | 3/2000 | McKay |
| 6,316,091 B1 | 11/2001 | Richart et al. |
| 6,511,510 B1 | 1/2003 | de Bruijn et al. |
| 6,616,698 B2 | 9/2003 | Scarborough |
| 6,626,950 B2 | 9/2003 | Brown et al. |
| 6,793,725 B2 | 9/2004 | Chow et al. |
| 6,991,803 B2 | 1/2006 | Sapieszko et al. |
| 6,994,726 B2 | 2/2006 | Lin et al. |
| 7,004,974 B1 | 2/2006 | Larsson et al. |
| 7,012,034 B2 | 3/2006 | Heide et al. |

(Continued)

FOREIGN PATENT DOCUMENTS

DE  196 10 715 C1  6/1997
EP  0 677 297 B1  12/2000

(Continued)

OTHER PUBLICATIONS

M. Bohner, G.H. van Lenthe, S. Grünenfelder, W. Hirsiger, R. Evison, R. Müller "Synthesis and characterization of porous β-tricalcium phosphate blocks", Biomaterials, vol. 26, Issue 31, Nov. 2005, pp. 6099-6105.

(Continued)

*Primary Examiner* — Elizabeth C Kemmerer
(74) *Attorney, Agent, or Firm* — Novak Druce Connolly Bove + Quigg, LLP

(57) ABSTRACT

The present invention relates to a sliceable composite bone repair material comprising a porous block-shaped ceramic scaffold and a stabilizing polymer disposed therein. Said ceramic scaffold is a synthetic ceramic material or a naturally-derived material. Additionally said scaffold comprises interconnected macropores.

13 Claims, 6 Drawing Sheets

(56) References Cited

U.S. PATENT DOCUMENTS

| | | | |
|---|---|---|---|
| 7,083,749 B2 | 8/2006 | Lin et al. | |
| 7,097,792 B2 | 8/2006 | Lin et al. | |
| 7,097,793 B2 | 8/2006 | Lin et al. | |
| 7,115,222 B2 | 10/2006 | Lin et al. | |
| 7,122,138 B2 | 10/2006 | Lin et al. | |
| 7,122,139 B2 | 10/2006 | Lin et al. | |
| 2003/0143258 A1 | 7/2003 | Knaack et al. | |
| 2004/0002770 A1* | 1/2004 | King et al. | 623/23.51 |
| 2004/0024466 A1 | 2/2004 | Heerklotz et al. | |
| 2004/0265350 A1 | 12/2004 | Sambrook et al. | |
| 2005/0119762 A1* | 6/2005 | Zilla et al. | 623/23.75 |
| 2005/0124720 A1 | 6/2005 | Rizzoli et al. | |

FOREIGN PATENT DOCUMENTS

| | | |
|---|---|---|
| EP | 1 080 700 A2 | 3/2001 |
| EP | 1 150 726 B1 | 11/2003 |
| EP | 1374922 A1 | 2/2004 |
| EP | 1457214 A1 | 9/2004 |
| EP | 1 305 056 B1 | 12/2005 |
| EP | 1609491 B1 | 12/2005 |
| EP | 1 642 600 A1 | 4/2006 |
| EP | 1 490 123 B1 | 6/2006 |
| EP | 1490123 | 9/2006 |
| EP | 1820522 A1 | 8/2007 |
| WO | WO 92/10218 A1 | 6/1992 |
| WO | WO 97/34546 A1 | 9/1997 |
| WO | WO 00/44808 A | 8/2000 |
| WO | WO 00/59559 A1 | 10/2000 |
| WO | WO 03/040235 A | 5/2003 |
| WO | WO 03/080144 A1 | 10/2003 |
| WO | WO 2004/011053 A1 | 2/2004 |
| WO | WO 2004/054633 A3 | 7/2004 |
| WO | WO 2005/018700 A1 | 3/2005 |
| WO | WO 2006/069388 A2 | 6/2006 |

OTHER PUBLICATIONS

A. Odgaard and H.J.G. Gundersen "Quantification of Connectivity in Cancellous Bone, with Special Emphasis on 3-D Reconstructions", Bone, vol. 14, Issue 2, Mar.-Apr. 1993, pp. 173-182.

Nov. 19, 2008 International Search Report in corresponding PCT/EP 2008/005340.

* cited by examiner

COMPOSITE BONE REPAIR MATERIAL

FIELD OF THE INVENTION

The present invention relates to a composite bone repair material comprising a porous block-shaped synthetic ceramic scaffold and a stabilizing polymer disposed therein.

BACKGROUND

The repair of bone defects can be facilitated by placing a bone repair material as a temporary substitute in the defect site, where a loss of natural bone has occurred. The bone repair material is meant to selectively promote and guide the regeneration of natural bone structures.

Both naturally-derived and synthetically-produced bone repair materials have been used to repair such defects. Naturally-derived materials include grafts made from bones. The bone may be harvested directly from the patient, as in autograft-based procedures, or it may be harvested from a suitable donor, surrogate, or cadaver, as in allograft- or xenograft-based procedures. Naturally-derived bone repair materials are usually prepared by acid extraction of most of the mineralized component to result in so called demineralized bone matrix (DBM). Examples for naturally-derived materials are Bio-Oss® of the mineral portion of bovine bone or Algipore® a porous calcium phosphate material of algae. Autologous bone is an ideal source of graft material, not only due to its biocompatibility, but also because natural bone grafts facilitate reossification of the defect site by promoting or conducting ingrowth of the patient's own bone tissue to the defect site. Autologous bone material inherently is osteoconductive and osteoinductive, two properties facilitating regeneration of natural bone structure. However, autograft bone implant procedures are costly and cause additional discomfort for the patient, as they typically require an additional surgery for harvesting the graft material, which may cause significant morbidity at the donor site. Autografts may also show pronounced resorption making the outcome of the augmentation unpredictable. Allogenic bone repair materials also unify osteoconductive and osteoinductive properties, but their origin raises possible pathogenic transfers and ethical issues. Similar concerns are brought up against xenogenic graft materials.

Alternatively, naturally-derived bone repair materials may be replaced by a completely synthetic bone repair material, which contains no organic residues. In contrast to naturally-occurring bone repair materials, synthetic bone repair materials are often less osteoconductive and hardly osteoinductive. Nevertheless, much research has been and still is directed toward improved synthetic bone repair materials.

In oral surgery and orthopedics, synthetic bone repair materials on a hydroxyapatite (HA) and/or tricalcium phosphate (TCP) basis are widely used. Depending on indications, they may be applied as granules or pre-fabricated blocks. U.S. Pat. No. 6,511,510 relates to a porous ceramic material from calcium phosphates obtained by a sintering process. The use of granular material allows treatment of a wide range of indications. For granular material, the ceramic block material is processed by steps such as rubbing, pounding and sieving afterwards (WO 04/054633). Although the granular materials are applied to a wide range of indications in terms of size and area, their suitability to treat large bone defects is limited, because they tend to migrate and as a result to be encapsulated. The augmented volume defined by the applied granules may collapse and fail to guide regrowth of the bone to its original dimensions. U.S. Pat. No. 7,012,034 describes a block-shaped bone augmentation material based on porous β-tricalcium phosphate.

Different approaches addressed the problem of providing a material with bone-like mechanical properties. In U.S. Pat. No. 6,994,726 a prosthetic bone implant is made of a hardened calcium phosphate cement having an apatitic phase as a major phase, which comprises a dense cortical portion bearing the majority of load, and a porous cancellous portion allowing a rapid blood/body fluid penetration and tissue ingrowth. Alternatively, EP 1457214 discloses a block shape organic-inorganic complex porous article with a superposed skin layer made of a degradable polymer with improved strength. The complex is mainly designed to be inserted between vertebral bodies.

To generally improve load bearing properties of bone repair materials, composite materials have been developed. EP 1374922 discloses a bioresorbable structure for use in the repair of bone defects comprising a porous bioceramic matrix of hydroxyapatite or tricalcium phosphate and a polymer disposed by compression moulding therein. WO 97/34546 describes a ceramic block with a plurality of channels filled containing an enforcing bio-resorbant polymer material. In order to improve their regenerative potential, bone repair materials have been supplemented with bone growth inducing agents. U.S. Ser. No. 10/271,140 (US2003/0143258A1) suggests a composite comprising demineralized bone matrix mixed with a stabilizing biodegradable polymer and a bone growth factor.

In a typical periodontal surgical bone repair procedure an incision is made in the gum tissue to expose a bone defect adjacent to a tooth root. Once the defect and root are debrided, a bone repair material, suspended in a suitable carrier is placed. The gum tissue is then closed, maintaining the repair material in place. Optionally, a barrier material may be utilized to retain the repair formulation in contact with the defect. Therefore, a bone repair material in periodontal surgery requires formulations that can be easily shaped to size and shape of the defect. WO 2004/011053 suggests a formulation with a putty consistency. Similarly, EP1490123 describes a kneadable and pliable bone replacement material on a granular calcium phosphate and hydrogel basis. When applied to the defect site, the formulation remains adhered thereto without migration or excessive expansion. These concepts however, do provide for a solid bone substitute material.

SUMMARY OF THE INVENTION

The problem of the present invention is therefore, to provide a bone repair material having osteoconductive and osteoinductive properties and which is easy to handle and suitable for treatment of large oral bone defects.

Surprisingly it was found that the composite bone repair material according to the present invention emulates the osteoconductive and the osteoinductive properties of autografts. Further, due to the combination of the porous block-shaped synthetic ceramic scaffold and the stabilizing polymer disposed therein, the composite has sufficient stability to prevent movement of the graft material and that it is strong enough is to withstand the forces within the implantation site, i.e. is resistant to mechanical stress. In addition, the material is not brittle and therefore sliceable. This means that the surgeon may bring the bone repair material into the desired shape by cutting it with the scalpel or process it with a bur. The bone repair material according to the present invention thus can be used in the treatment of large bone defects, such as critical size defects in oral indications that do not heal spontaneously. More particularly, the bone repair material of the invention is especially preferred upon enhancing treatment of oral bone defects such as bone loss from moderate or severe periodontitis, bony defects of the alveolar ridge, tooth extraction sites, or pneumatized (expanded) sinus.

The composite bone repair material according to the present invention comprises a porous block-shaped scaffold and a stabilizing polymer disposed therein. The porous block-shaped scaffold can be a synthetic ceramic material or a naturally-derived material. In a preferred embodiment said porous block-shaped scaffold the synthetic ceramic material comprises calcium phosphate. In further preferred embodiment the synthetic ceramic material comprises a calcium phosphate selected from the group consisting of apatite and tricalcium phosphate or a mixture thereof. Further said ceramic scaffold comprises interconnected macropores.

Ceramic scaffold material composed of calcium phosphates, namely apatite and tricalcium phosphate (TCP) or combinations thereof, are efficient bone substitutes that enhance bone ingrowth. Eventually, the material gets resorbed and substituted by bone. Hydroxyapatite and β-tricalcium phosphate, and combinations thereof are especially preferred. These materials can be manufactured with well defined reproducible morphologies with respect to size and porosity (see FIG. 1)

The scaffold material according to the present invention has a porous morphology. Said ceramic scaffold material is a highly porous calcium phosphate with interconnected pores of a size range that allows fast ingrowth of natural bone. Methods to characterize calcium phosphate blocks with regard to the porosity have been described in Biomaterials, 2005 November; 26(31):6099-105.

Two samples of scaffold material as depicted in FIG. 1 were analyzed by micro-computed tomography (µCT). Morphometric measures are summarized in Table 1.

polymeric matrix with a determined pore structure or spherical objects are coated with the slurry. After drying the slurry, the ceramic material undergoes a sintering process at high temperatures between 800° C. and 1300° C., depending on the degree of cristallinity desired. During sintering the pore forming material is burned out and a porous ceramic scaffold remains (FIG. 1). Depending on the process and the pore forming agent or material, the porosity of the ceramic block-shaped material can be adjusted to result in a desired distribution interconnectivity of pores of various sizes. They can be classified as nanopores (diameter below 1 µm), micropores (diameter between 1 and 100 µm) and macropores (diameter above 100 µm). For the purpose of tissue regeneration, a substantial amount of interconnected micropores and macropores is desired in order to allow cells to migrate into the scaffold material. Micropores are sufficient to allow nutrient and metabolic product transport. In a preferred embodiment of the invention, the diameter of the pores lies between 0.05 and 750 µm. More preferably, the diameter of the micropores is between 5 and 100 µm and the diameter of the macropores is between 100 and 1000 µm. Most preferably, the diameter of the micropores is between 10 and 70 µm and the diameter of the macropores is between 100 to 750 µm. The porosity of the preferred scaffold material according to this invention has mean pore diameter between 300 and 600 µm. The preferred embodiment further has highly interconnected pores. The interconnectivity can be defined as connective density (equivalent to the terms connectivity or interconnectedness) as described in *Bone*, 1993 March-April; 14(2):173-82. The scaffold material according to this invention has a connectivity, which is above 20 per mm$^3$. In terms of connections per pore, which is equal to the ratio of interconnectedness and the number of pores per volume, the scaffold material according to this invention has a connectivity per pore, which at least 2, more preferably above 3. As described

TABLE 1

Morphometric measures for two samples

| Scaffold Volume [%] | Pore Volume [%] | Surface Density [1/mm] | Specific Surface Density [1/mm] | Mean Pore diameter [mm] | Interconnectivity [1/mm$^3$] | Interconnections per pore |
|---|---|---|---|---|---|---|
| 13.662 | 86.339 | 5.184 | 38.841 | 0.496 | 48.338 | 3.082 |

For the preferred scaffold material according to this invention the total porosity lies in the range of 75 to 95%, preferably from 80 to 95%. Porosity is the percentage of void space per volume unit of scaffold material. High porosity usually results in a large specific surface density, which is one important property increasing primary liquid absorption and protein adsorption throughout the whole material. Specific surface density is defined as the scaffold surface per scaffold volume. The preferred scaffold material according to this invention has a specific surface density of at least 20/mm, more preferably above 30/mm. Moreover, the preferred ceramic scaffold material facilitates optimum nutrient and oxygen supply, neo-vascularisation, cell immigration, colonization and bone deposition. Finally, the material will be integrated in newly formed bone and will eventually be degraded and replaced by natural bone.

The porous structure may be obtained by various processes. Usually a ceramic powder is suspended in an aqueous solution to result in a slurry. To form a porous structure, a pore forming agent may be added. Alternatively a sponge-like above, the porosity does not need to be of random distribution, but may be obtained by a highly repeated spacing structure such as tubuli. A tubular structure with a suitable stabilizing polymer may be preferred, if high mechanical strength is required.

In addition to the composition and porosity, a suitable architecture of the block-shaped ceramic scaffold material may further enhance bone regeneration and improve the handling properties. A first portion of the block oriented to the remaining bone, which needs to be augmented, preferably has a cancellous structure with a high proportion of macropores, thereby facilitating the integration into bone tissue. A second portion of the block-shaped ceramic scaffold material oriented to the surrounding soft tissue preferably has dense structure in order to reduce the risk of soft tissue ingrowth into area of bone augmentation. Therefore, the ceramic scaffold material subject to this invention preferably is manufactured to contain a gradient in its porosity and/or crystallinity and/or ceramic composition In oral surgery, bone regeneration in large bone defects is performed by means of bone block fixation techniques. Such fixation techniques typically include drilling and fixing an autologous bone block with a screw at the defect site. It would be desirable to provide a synthetic bone block, which has physical properties similar to those of autologous bone, so the conventional fixation techniques could be applied. Therefore the second portion of the block-shaped ceramic scaffold material preferably has also an enhanced mechanical strength similar to the cortical portion of a natural bone, resisting pressures of up to about 110-170 MPa, and is sufficiently rigid to be fixed by screws. In a basic form of this embodiment of the invention, the ceramic scaffold material has at least one rigid layer on the surface portion, which is obtained by dipping the portion into desired second slurry of ceramic bone repair material. The peripheral portion can comprise one or several preformed fixation holes.

The ceramic scaffold material according to the present invention is block-shaped and can be applied to any large bone defect and which has superior handling properties. The composite bone repair material of this invention is based on a ceramic scaffold material in pre-manufactured block shape. Block-shaped shall mean, that the ceramic scaffold material is based on a solid body, which exceeds the dimensions of conventional granular bone repair material for oral applications and is designed to substantially fill a bony defect. Block-shaped shall encompass any dimensions and shapes desired by a practitioner to treat a bony defect. Due to the added or embedded stabilizing polymer, the composite bone repair material can be adjusted to the individual defect size and shape with a scalpel or with dental burs during surgery. That means that the composite bone repair material according to the present invention is sliceable, and in contrast to the materials known in the art not brittle, which is an enormous advantage. For use in lateral (horizontal) and vertical jaw ridge defects, dimensions up to a volume of 10 cm$^3$, preferably between 0.1 and 4 cm$^3$, typically about 6×6×12 mm have proven to be suitable for most defects. Alternatively, several units of block-shaped composite bone repair material can be used in a kit in a building block system with differently sized blocks.

As mentioned above the bone repair material according to the present invention comprises a stabilizing polymer. Said stabilizing polymer may be naturally-derived or synthetically produced. In one embodiment, the polymer is formed of proteins, preferably proteins naturally present in the patient, into which the composite mesh is to be implanted. A particularly preferred natural polymeric protein is fibrin, although polymers made from other proteins, such as collagen and gelatin can also be used. Polysaccharides as hyaluronic acid or glycoproteins may also be used to form the polymeric matrix.

Suitable synthetic polymers include polyoxyalkylenes, poly(vinyl alcohol), poly(ethylene-co-vinyl alcohol), poly(urethane)s, poly(hydroxyalkyl acrylate)s, poly(hydroxyalkyl methacrylate)s, poly(acrylic acid), poly(methacrylic acid), poly(ethylene-co-acrylic acid), poly(alkyloxazoline)s, poly(vinyl pyrrolidone), poly(ethylene-co-vinyl pyrrolidone), poly(maleic acid), poly(ethylene-co-maleic acid), poly(acrylamide), and poly(ethylene oxide)-co-(propylene oxide) block copolymers.

A particularly preferred polymer or precursor substance is linear or branched polyethylene glycol. It could be shown that ceramic scaffold material according to the present invention which is soaked with a linear polyethylene glycol (PEG) polymers of a suitable molecular weight that it has a waxy consistency, results in a composite with excellent handling properties. The concentration of a linear PEG is adjusted to obtain the desired consistency. When using short linear PEG molecules of a molecular weight of about 1 kDa, a concentration of up to 100% may be required. For larger linear PEG molecules of a molecular weight up to 1000 kDa PEG, a aqueous solution of 10% may be sufficient. The bone scaffold material is no longer brittle but has a malleable consistency and can be shaped with a scalpel, which is appreciated by the practitioner for fitting the block to the bone defect site. Further it could be shown, that a water-swollen, crosslinked PEG matrix (PEG hydrogel) further improves the mechanical properties of the bone scaffold material and is easier to apply. Ideally, the bone scaffold material is soaked with precursor substances of the stabilizing polymer prior to the polymerization reaction. The polymerization within the porous structure of the bone scaffold material then forms a composite mesh of the two materials.

The mechanism leading to a polymeric network can be ionic, covalent, or any combination thereof, or swelling of one or more polymeric material(s), or physical crosslinks, e.g. by crosslinking points formed through aggregation of endblocks through phase or solubility differences.

However, the preferred stabilizing polymers according to this invention are crosslinked polyethylene glycols (PEG) hydrogels formed by a self selective addition reaction between two precursors as described in EP 1 609 491.

The use of PEG hydrogels in a composite bone repair material subject to this invention has many advantages. PEG hydrogels are well known for their excellent biocompatibility and their hydrophilicity. Such hydrogels are permeable for aqueous biologicals fluids and therefore allow diffusion of nutrients required in tissue regeneration.

The hydrogels preferred as stabilizing polymer in this invention are based on the base catalyzed Michael type addition between the conjugated unsaturated group or the conjugated unsaturated bond of a first precursor A and the thiol group of a second precursor B. The resulting linkage is unstable and hydrolyzed in contact with water. The rate of the hydrolysis reaction depends on the temperature and the value of the pH, which is 7.4 in most tissues. When sufficient bonds have hydrolyzed, the crosslinked network degrades or breaks down. Therefore, the time of degradation of the network can be influenced by the number of hydrolysable bonds present per unit of volume.

The precursors forming the stabilizing polymer are dissolved or suspended in aqueous solutions. Since no organic solvents are necessary, only aqueous solutions and/or suspensions are present. These are easy to handle and do not require any laborious precautions as might be the case if organic solvents were present. Furthermore, organic solvents are an additional risk for the health of the staff and the patients exposed to these solvents. The present invention eliminates said risk. The gelation of the stabilizing polymer is completed within minutes, starting at the time of mixing.

Below, a preferred stabilizing polymer from PEG formed by reaction of precursors A and B is described in more detail. The first precursor A comprises a core which carries n chains with a conjugated unsaturated group or a conjugated unsaturated bond attached to any of the last 20 atoms of the chain. In a preferred embodiment said conjugated unsaturated group or conjugated unsaturated bond is terminal. The core of the first precursor A can be a single atom such as a carbon or a nitrogen atom or a small molecule such as an ethylene oxide unit, an amino acid or a peptide, a sugar, a multifunctional alcohol, such as pentaerythritol, D-sorbitol, glycerol or oligoglycerol, such as hexaglycerol. The chains are linear polymers or linear or branched alkyl chains optionally comprising heteroatoms, amide groups or ester groups. Preferably the chain is a polyethylene glycol. Beside the chains, the core of precursor A may be additionally substituted with linear or branched alkyl residues or polymers which have no conjugated unsaturated groups or bonds. In a preferred embodiment the first precursor A has 2 to 10 chains, preferably 2 to 8, more preferably 2 to 6, most preferably 3 to 6 chains. The conjugated unsaturated bonds are preferably acrylates, acrylamides, quinines, 2- or 4-vinylpyridiniums, vinylsulfone, maleimide or itaconate esters of formula Ia or Ib

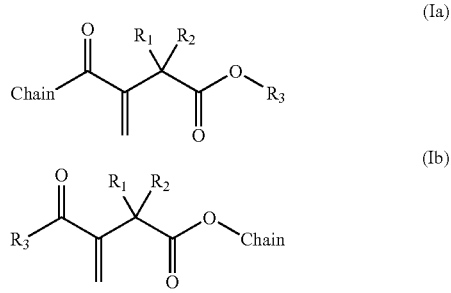

wherein $R_1$ and $R_2$ are independently hydrogen, methyl, ethyl, propyl or butyl, and $R_3$ is a linear or branched $C_1$ to $C_{10}$ hydrocarbon chain, preferably methyl, ethyl, propyl or is butyl. Preferably the precursor A is a PEG-acrylate with 2 to 6 chains (2-arm to 6-arm PEG-acrylate).

The second precursor B comprises a core carrying m chains each having a thiol or an amine group attached to any of the last 20 atoms at the end of the chain. For example a cysteine residue may be incorporated into the chain. Preferably the thiol group is terminal. The core of the second precursor B can be a single atom such as a carbon or a nitrogen atom or a small molecule such as an ethylene oxide unit, an amino acid or a peptide, a sugar, a multifunctional alcohol, such as pentaerythritol, D-sorbitol, glycerol or oligoglycerol, such as hexaglycerol. The chains are linear polymers or linear or branched alkyl chains optionally comprising heteroatoms, esters groups or amide groups. Preferably the chain is a polyethylene glycol. In a preferred embodiment the second precursor B has 2 to 10 chains, preferably 2 to 8, more preferably 2 to 6, most preferably 2 to 4 chains. Preferably the precursor B is a PEG-thiol with 2 to 4 chains (2-arm to 4-arm PEG-thiol).

The first precursor A compound has n chains, whereby n is greater than or equal to 2, and the second precursor B compound has m chains, whereby m is greater than or equal to 2. The first precursor A and/or the second precursor B may comprise further chains which are not functionalized.

The sum of the functionalized chains of the first and the second precursor, that means m+n, is greater than or equal to 5. Preferably the sum of m+n is equal to or greater than 6 to obtain a well formed three-dimensional network. Such molecules having a core and two or more end groups are also referred to as multi-arm polymers.

Beside the number of chains, their length is a crucial parameter to adjust the mechanical properties of the bone composite material subject to this invention. The number of atoms in the backbone connecting two adjacent crosslinking points is at least about 20 atoms, preferably between 50 and 5000 atoms and more preferably between about 50 and 2000 atoms and ideally between 100 and 750 atoms. A crosslinking point is here defined as a point in which 3 or more backbone chains of the polymer network are connected.

The mechanical strength of the bone composite material can be further enhanced by embedding one or more additional stabilizing polymers, fibrous or filamentous supplements such as carboxy methyl cellulose, alginates, xanthan gum etc.

In a further embodiment of the present invention the stabilizing polymer is provided with a degradability by enzymatic degradation sites. An accordingly designed polymer will not degrade and lose its stabilizing function, unless ingrowing cells are present to replace the synthetic structure of the polymer. In this embodiment, the core of precursor B comprises a peptide which comprises one or more enzymatic degradation sites. Preferred enzymatic degradable hydrogels contain metalloproteinase oligopeptides integrated in their backbone instead of a hydrolytically instable bond as described in detail in WO03040235A1.

Such a stabilizing polymer, such as PEG hydrogel is preferably introduced into the pores of the bone block by soaking the block-shaped synthetic ceramic scaffold with a PEG hydrogel formulation at room temperature. One possibility to do this is to mix the hydrogel precursors and then, before the gel point is reached, apply the mixture onto the block and allow it to be absorbed by the block and gel inside the pores of the block. This procedure can be performed by the surgeon before adapting the block to the desired shape.

In a further embodiment of the present invention the stabilizing polymer disposed in the synthetic ceramic scaffold is at the same time a matrix for sustained release of one or several bioactive agents, which promote the osteoconductive and/or osteoinductive properties of the composite bone repair material. As used herein, a bioactive agent is not limited by its origin or the way it is produced and therefore can be extracted, synthetically or recombinantly produced and may have been subject to further processing or purification, such as but not limited to, splicing, fragmentation, enzymatic cleavage or chemical modification.

Examples of suitable biologically active agents are BMPs, PTH, VEGF, Enamel Matrix Derivatives (EMD), TGF-beta, IGF, Dentonin, Adrenomedullin (ADM), FGF, PDGFBB, IGF, PGE2, EP2, L1 (and derivatives), HIF-1α∆ODD (oxygen-independent domain), cell recognition sequences such as RGD, KRSR, H-Gly-Cys-Gly-Arg-Gly-Asp-Ser-Pro-Gly-$NH_2$ or derivatives thereof.

Also extracellular matrix proteins such as fibronectin, collagen, laminin may be used as bioactive agents. These peptides and proteins may or may not comprise additional cystein. Such cystein facilitates the covalent attachment of the peptides and proteins to the preferred form of stabilizing polymer as described above.

Particularly preferred is a peptide comprising the first 34 amino acids of PTH. This peptide may contain an additional cystein, which facilitates the covalent attachment of the peptide to the composite bone repair material. In a further preferred embodiment the bioactive agent is selected from the group of EMDs consisting of amelogenin, amelin, tuftelin, ameloblastin, enamelin and dentin.

The preferred stabilizing polymers previously described are also suitable for delivery or of bioactive agents. The bioactive agent may be covalently bound to the stabilizing polymer, e.g., this can be achieved by a thiol moiety present in the bioactive agent which reacts with the conjugated unsaturated group or bond present in precursor A upon mixing. A thiol moiety is present, e.g. in the amino acid cystein. This amino acid can easily be introduced in peptides, oligo-peptides or proteins. The bioactive agent is subsequently released from the stabilizing polymer as the unstable linkage hydrolyzes.

Alternatively, the preferred embodiments of the stabilizing polymer described above allow the active agents to be simply entrapped or precipitated into the composite bone repair material. The bioactive agent can be added when mixing the other components of the composition. The bioactive agent is then released by diffusion after degradation of the hydrogel. It is also possible to adsorb the bioactive agent on the ceramic scaffold material prior to the soaking with the solutions comprising the first precursor A and the second precursor B.

Kits also fall within the scope of the present invention. The kit comprises at least (i) a block-shaped ceramic scaffold and (ii) a stabilizing polymer. In a further embodiment the kit comprises at least (i) a block-shaped ceramic scaffold, (II) a precursor A, such as a multi-arm PEG-acrylate, and (III) a precursor B, such as a multi-arm PEG-thiol, which are each individually stored. Another kit comprises (I) a block-shaped ceramic scaffold, (II) a stabilizing polymer, and (III) a bioactive agent. In addition the kit further comprises one or several if required by the precursors and/or the bioactive agent. A suitable activator would be an aqueous solution of triethanolamine with HCl at pH of 7.4-9.0. The kit may also comprise more than one bioactive agent and more than two precursors. It is also possible that the kit comprises certain components in premixed form. The precursors can be stored in dry form or in a suitable solvent (e.g. 0.04% acetic acid). A suitable buffer solution is added immediately prior to application. The precursors are preferably stored in a dry form. The bioactive agent can be (pre-) adsorbed to the ceramic scaffold. Further, the bioactive agent can be stored in a dry (lyophilized) form or in an aqueous solution which is suitably buffered.

DETAILED DESCRIPTION

Examples

Example 1

A slurry of well dispersed hydroxyapatite powder obtained from Merck S. A., was prepared in an alcohol/binder/plasticizer solution and a polyurethane foam was impregnated with this slurry. The composition of the binder/plasticizer mix was as follows: 90 g polyethylene glycol #6000; 150 g poly-vinyl butyral; 240 g ethanol absolute; 600 g trichloroethylene. The slurry was prepared using the following batch composition: 70 g hydroxyapatite; 50 g ethanol absolute; 1 g emphos PS-21A deflocculant; 36 g binder/plasticizer mix. A commercially available high porosity, low density polyurethane foam was used (from Recticel, Belgium).

The foam was first immersed into the slurry and repeatedly compressed and expanded to ensure complete coverage of all pore walls. The excess slurry was then removed and the coated foam allowed to dry. The ceramic artefact was formed by heating the impregnated foam in stages to ensure the complete burn-out of all organic matter and finally sintering the hydroxyapatite using the following firing schedule: 90° C./h to 250° C., hold for 2 hours; 50° C./h to 650° C. hold for 5 hours; 200° C./h to 1200° C., holding for 2 hours; cooling at 200° C./h to ambient.

The ceramic scaffold material was cut into blocks of 1×1×2 cm$^3$.

Example 2

Figure 1:
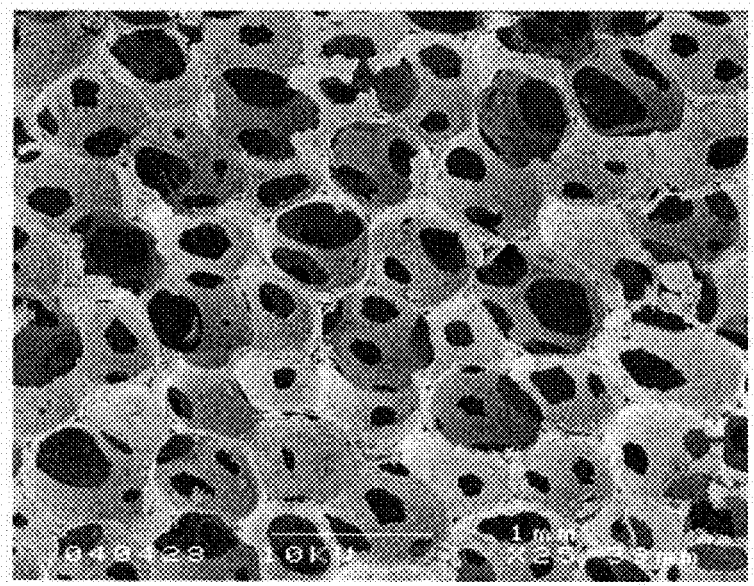
FIG. 1 shows a sponge-like structure of the ceramic scaffold material.
Figure 2:
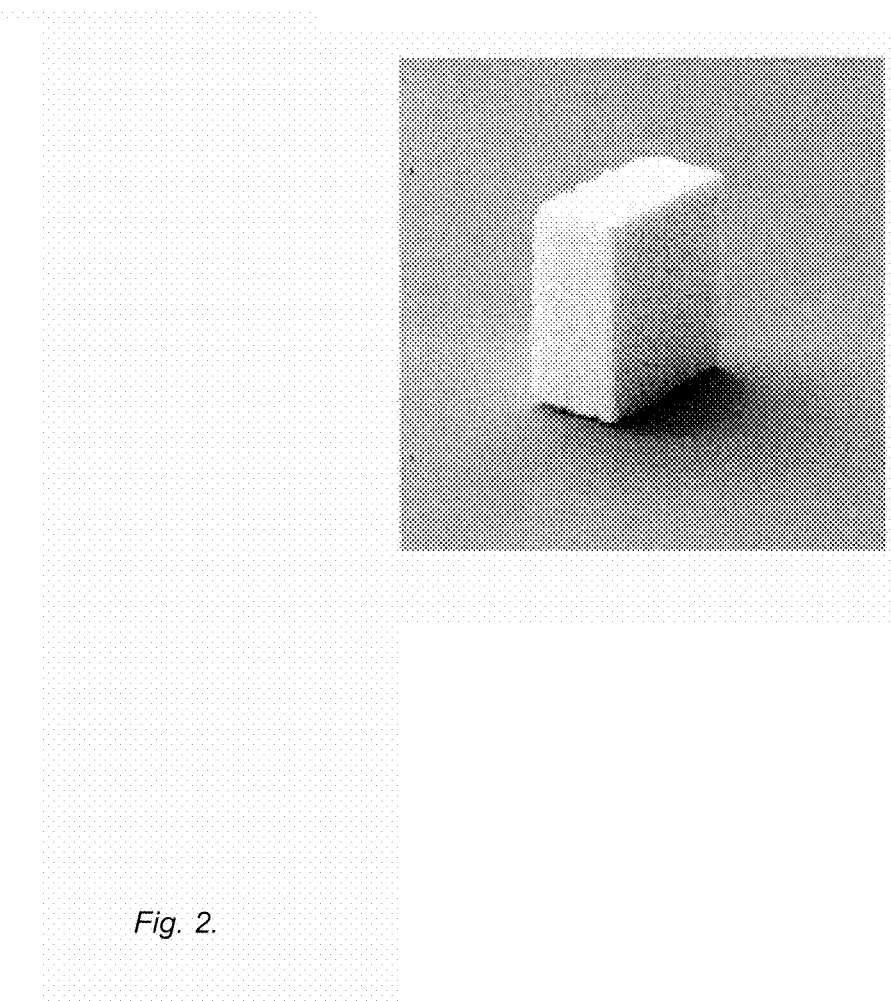
FIG. 2 shows a block-shaped ceramic scaffold material.
Figure 3:
FIG. 3 shows a ceramic scaffold material without stabilizing polymer cut with a scalpel.
Figure 4:
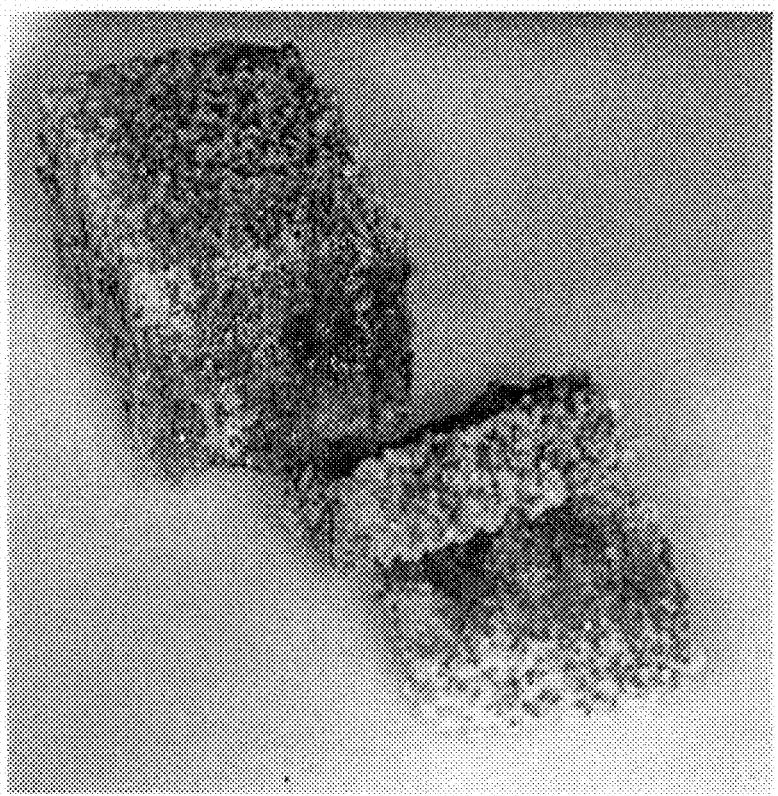
FIG. 4 shows a ceramic scaffold material with PEG gels after polymerization cut with a scalpel.
Figure 5:
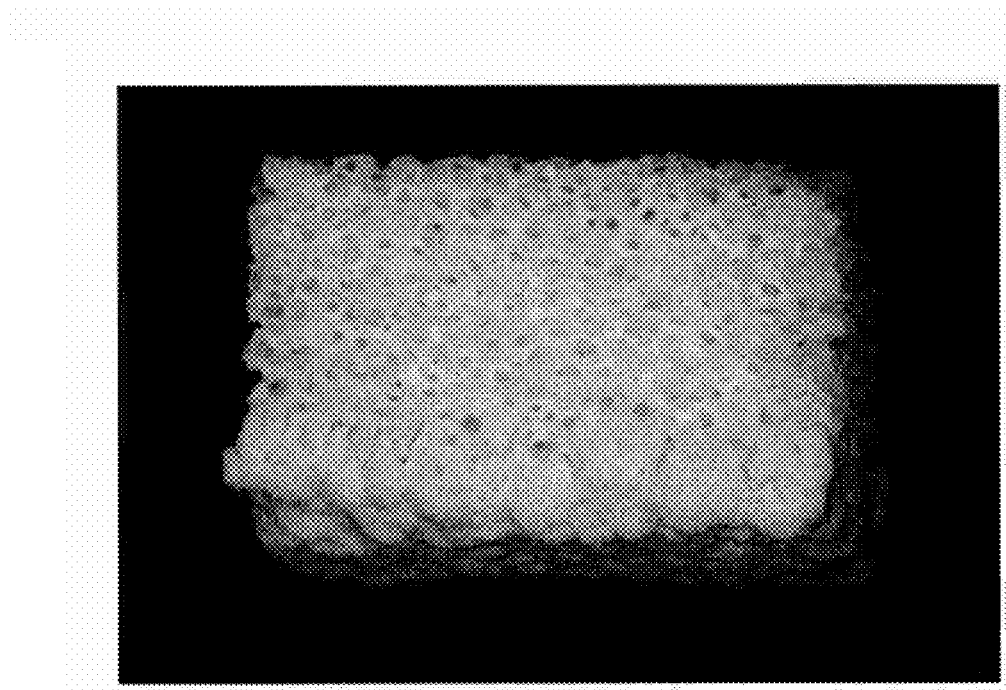
FIG. 5 shows a ceramic scaffold material with a dense layer of hydroxyapatite.

The aim of this example was to prepare a block-shaped ceramic scaffold material with a rigid portion. Blocks were prepared according to Example 1 with the difference, that before the final sintering step, one side of the block was dipped about 1 mm deep into a slurry of pure hydroxyapatite. Thereby, the pores on the dipped side of the sponge were completely filled with slurry. (FIG. 4)

Example 3

65.5 mg (0.0336 mmol thiol) of HS-PEG-SH 3.4 k (Nektar, Huntsville, Ala., USA) were dissolved in 0.685 ml of 0.05% acetic acid and 130.5 mg (0.0330 mmol acrylate) of 4-arm PEG-acrylate 15 k (Nektar, Huntsville, Ala., USA) were dissolved in 0.620 ml of 0.05% acetic acid containing 100 ppm of methylene blue. Both PEG solutions were mixed with 0.500 ml of a 0.4 M triethanolamine/HCl buffer (pH 8.85) and pipetted slowly onto a bone block from example 1 measuring 1×1×2 cm$^3$. The liquid was almost completely taken up by the porous block and formed a gel in the pores of the block in ca. 3 minutes at 25° C. The block could then be easily cut using a scalpel and clean cutting surfaces were obtained. Cutting a block with empty pores caused it to crumble (FIG. 4).

Example 4

32.4 mg (0.0164 mmol thiol) of HS-PEG-SH 1.8 k (Nektar, Huntsville, Ala., USA) were dissolved in 0.470 ml of 0.10 M triethanolamine/HCl pH 7.4 and mixed with 50 μl of 10 mg/ml hPTH$_{1-34}$. The gelation process was started with 66.0 mg (0.0166 mm acrylate) of PEG-acrylate, dissolved in 0.10 M triethanolamine/HCl pH 7.4. Four ml PBS containing 500 μg PTH was added to a final incubation volume of 5 ml (100 μg PTH/ml). The solutions were incubated at 37° C. (rotation mixer) and from the same tube (15 ml, plastic standard tubes) 50 μl of sample was collected (1.5 ml micro tubes, 72.690.200, Sarstedt) for immediate HPLC analysis (single analysis). No buffer was added to compensate the loss of sample volume during the whole experiment. The positive and negative controls were analysed before and after that all of the test solutions were analysed.

The samples were analysed (5 μl) on an TSK SSW2000 (18674, 4.6×300 mm, 4 μm, TosoHaas, Gmbh, Germany) in the mobile phase (30% acetonitrile [co3c11x, Labscan], 0.9% NaCl) at a flow of 0.3 ml/min, delivered from a HPLC system (pu880, Jasco Corporation). The peaks were detected as measured absorbance at 215 nm (online UV-detector, Jasco 1575) and the peak-areas were integrated.

TABLE 2

Retention of PTH (raw data from HPLC)

| Assay time (hours) | PTH concentration (area) | PTH conc. (% positive ctrl) |
|---|---|---|
| 0 | 62 | 97.3 |
| 1 | 255 | 88.7 |
| 15 | 391 | 82.7 |
| 22 | 658 | 70.8 |

TABLE 2-continued

Retention of PTH (raw data from HPLC)

| Assay time (hours) | PTH concentration (area) | PTH conc. (% positive ctrl) |
|---|---|---|
| 39 | 791 | 65 |
| 46 | 883 | 60.9 |
| 66 | 986 | 56.3 |
| 90 | 1086 | 51.9 |
| 114 | 1354 | 40 |
| 138 | 1532 | 32.2 |
| 354 | 1701 | 24.7 |
| Positive ctrl | 2258 | NA |
| Negative ctrl | 0 | NA |

Figure 6:
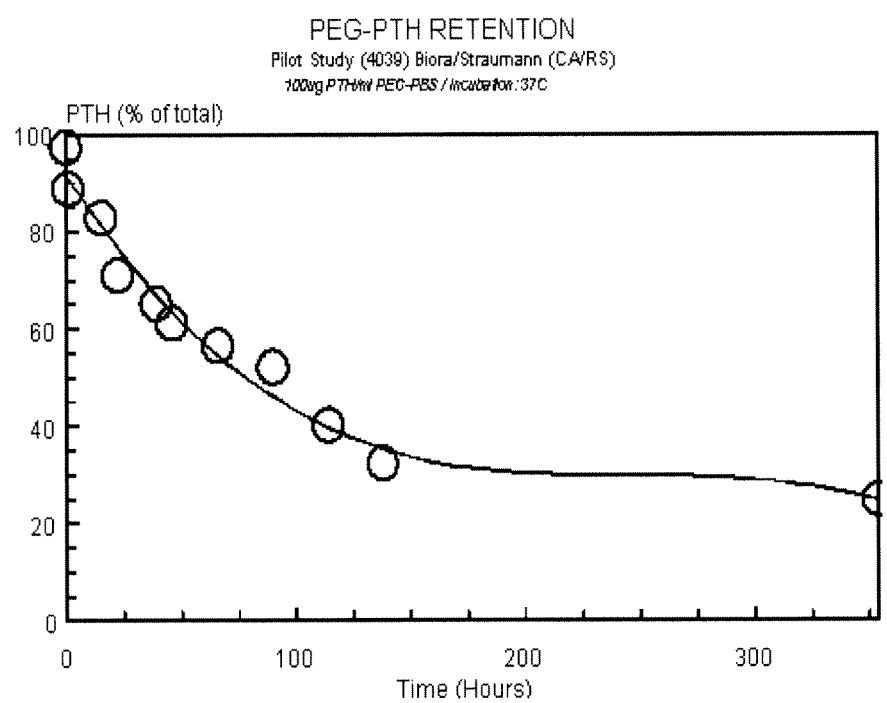
FIG. 6 shows a retention and release of PTH as bioactive agent from a stabilizing PEG polymer.

The data showed that PTH (1-34) was retained by the Straumann PEG-gel, 50% after 80 hours and 30% after 300 hours. The incubation was done in a horizontal rotation mixer (FIG. 6).

The invention claimed is:

1. A sliceable composite bone repair material comprising:
a porous block-shaped scaffold comprising a bone substitute material comprising a synthetic ceramic material, and wherein said scaffold comprises interconnected macropores; and
a stabilizing polymer disposed therein, wherein the stabilizing polymer is a degradable polyethylene glycol hydrogel formed by a cross-linking Michael-type addition reaction of at least two precursor molecules, wherein said cross-linking reaction forms an ester linkage between the at least two precursor molecules, and wherein said hydrogel is degradable in water.

2. Composite bone repair material of claim 1 wherein the scaffold is a synthetic ceramic material comprising a calcium phosphate.

3. Composite bone repair material of claim 2 wherein the calcium phosphate is selected from the group consisting of hydroxyapatite and tricalcium phosphate or a mixture thereof.

4. Composite bone repair material according to claim 1 wherein the ceramic scaffold has a total porosity between 75% and 95%.

5. Composite bone repair material according to claim 1 wherein the ceramic scaffold has at least a second portion with enhanced mechanical strength similar to cortical bone.

6. Composite bone repair material according to claim 1 further comprising a bioactive agent.

7. Composite bone repair material of claim 6, wherein the bioactive agent is released from the stabilizing polymer.

8. Composite bone repair material of claim 6, wherein the bioactive agent is selected from the group of parathyroid hormone, bone morphogenic protein and enamel matrix derivatives.

9. A device for the treatment of oral bone defects including the composite bone repair material of claim 1.

10. A kit for preparing a composite bone repair material according to claim 1 comprising the porous block-shaped synthetic ceramic scaffold and the stabilizing polymer.

11. A kit according to claim 10 comprising:
a) the porous block-shaped synthetic ceramic scaffold;
b) a multi-arm PEG-thiol;
c) a multi-arm PEG-acrylate, wherein the total number of arms is equal or larger than five; and
d) buffers for the multi-arm PEG-thiol and multi-arm PEG-acrylate.

12. A kit according to claim 10 additionally comprising a bioactive agent.

13. A kit according to claim 11 additionally comprising a bioactive agent premixed either with the multi-arm PEG-thiol or with the multi-arm PEG-acrylate.

* * * * *

UNITED STATES PATENT AND TRADEMARK OFFICE
CERTIFICATE OF CORRECTION

PATENT NO. : 8,574,611 B2
APPLICATION NO. : 12/667496
DATED : November 5, 2013
INVENTOR(S) : Seibl et al.

Page 1 of 1

It is certified that error appears in the above-identified patent and that said Letters Patent is hereby corrected as shown below:

On the Title Page, Item (73)

Please add the Second Assignee:

-- CAM Bioceramics B.V., Leiden (NL) --

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,574,611 B2                                                                 Page 1 of 1
APPLICATION NO. : 12/667496
DATED            : November 5, 2013
INVENTOR(S)      : Seibl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this
Twenty-second Day of September, 2015

Michelle K. Lee
*Director of the United States Patent and Trademark Office*